(12) United States Patent
Paul, Jr.

(10) Patent No.: US 7,533,696 B2
(45) Date of Patent: May 19, 2009

(54) ONE-WAY MEDICAL VALVE APPARATUS

(75) Inventor: Ram H. Paul, Jr., Bloomington, IN (US)

(73) Assignee: Cook Critical Care Incorporated, Bloomington, IN (US)

(*) Notice: Subject to any disclaimer, the term of this patent is extended or adjusted under 35 U.S.C. 154(b) by 549 days.

(21) Appl. No.: 11/183,423

(22) Filed: Jul. 18, 2005

(65) Prior Publication Data

US 2006/0016497 A1 Jan. 26, 2006

Related U.S. Application Data

(60) Provisional application No. 60/589,676, filed on Jul. 21, 2004.

(51) Int. Cl.
*F16K 15/14* (2006.01)
(52) U.S. Cl. .................. 137/846; 137/843; 604/247
(58) Field of Classification Search .......... 137/843, 137/844, 845, 846; 604/247
See application file for complete search history.

(56) References Cited

U.S. PATENT DOCUMENTS

| | | | |
|---|---|---|---|
| 2,594,525 | A | 4/1952 | Walden et al. |
| 3,463,159 | A | 8/1969 | Heimlich |
| 3,556,138 | A * | 1/1971 | D'Urso .................. 137/512.15 |
| 3,967,645 | A * | 7/1976 | Gregory .................... 137/846 |
| 4,103,689 | A | 8/1978 | Leighton |
| 4,535,818 | A * | 8/1985 | Duncan et al. .............. 137/846 |
| 4,966,197 | A | 10/1990 | Jaron et al. |

(Continued)

FOREIGN PATENT DOCUMENTS

EP 0 260 543 A1 3/1988

(Continued)

OTHER PUBLICATIONS

Dewey J. Conces, Jr. M.D., F.C.C.P.; Robert D. Tarver, M.D., F.C.C.P.; W. Cory Gray, M.D.; and Elizabeth A. Pearcy, M.D. "Treatment of Pneumothoraces Utilizing Small Caliber Chest Tubes" *Chest* 94/1 Jul. 1985.

(Continued)

*Primary Examiner*—Kevin L Lee
(74) *Attorney, Agent, or Firm*—Brinks Hofer Gilson & Lione

(57) ABSTRACT

A one-way valve apparatus for use in draining fluid from a patient comprises a housing having an inlet end, an outlet end and a valve-receiving chamber therebetween. A valve is positioned in the chamber. The valve has an inlet end, an outlet end and a fluid pathway extending therebetween. The valve is made up of first and second generally flat elongated members joined along respective longitudinal edges. The valve inlet end is engaged with the housing inlet end to comprise an open end for receiving fluid to be drained. The valve outlet end is in a normally closed position. The valve is adapted to partially open to permit drainage of fluid received through the pathway, and to return to the normally closed position upon drainage of the fluid. The valve outlet end communicates with the housing outlet end such that the drained fluid passes from the valve outlet end through the housing outlet end. The valve may be formed from an elastomeric material, and may be provided with a lubricious filler and/or a lubricous coating.

17 Claims, 3 Drawing Sheets

U.S. PATENT DOCUMENTS

| | | | |
|---|---|---|---|
| 5,073,168 A | 12/1991 | Danforth | |
| 6,044,859 A * | 4/2000 | Davis | 137/15.19 |
| 2008/0066815 A1 * | 3/2008 | Anderson | 137/846 |

FOREIGN PATENT DOCUMENTS

| FR | 1.577.117 A | 8/1969 |
|---|---|---|

OTHER PUBLICATIONS

E. Nicholas Sargent, M.D. and A. Franklin Turner, M.D. "Emergency Treatment of Pneumothorax" *The American Journal of Roentgenology, Radium Therapy and Nuclear Medicine* vol. CIX, No. 3 Jul. 1970.

\* cited by examiner

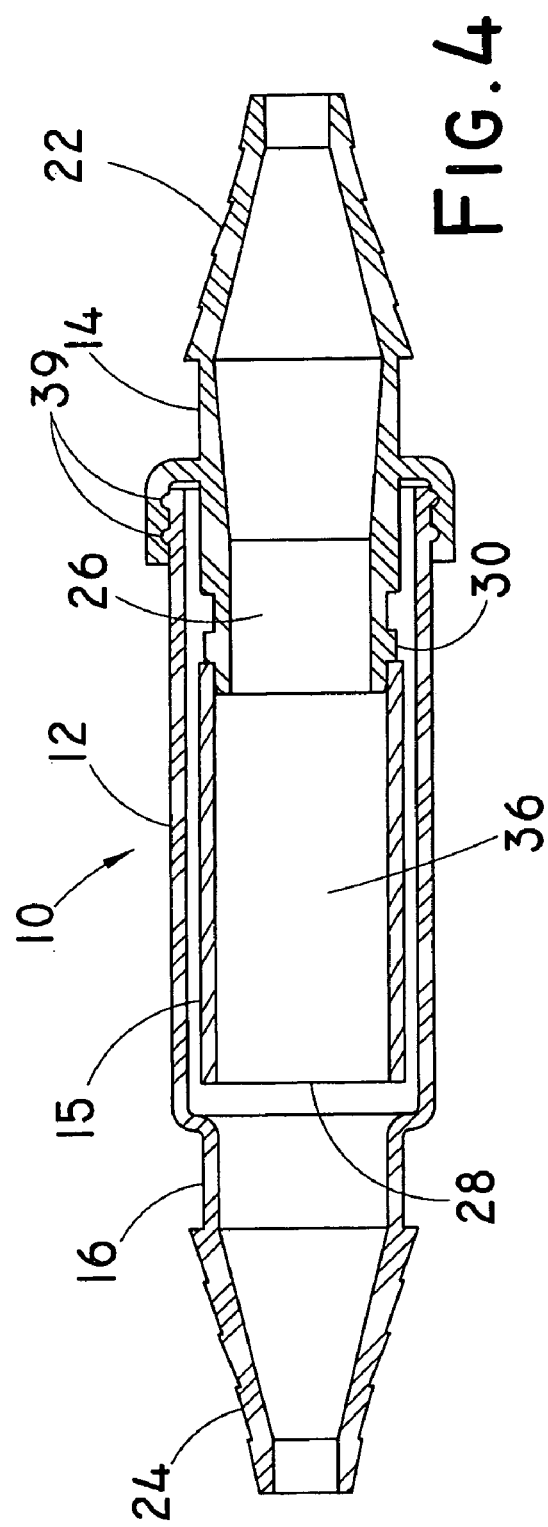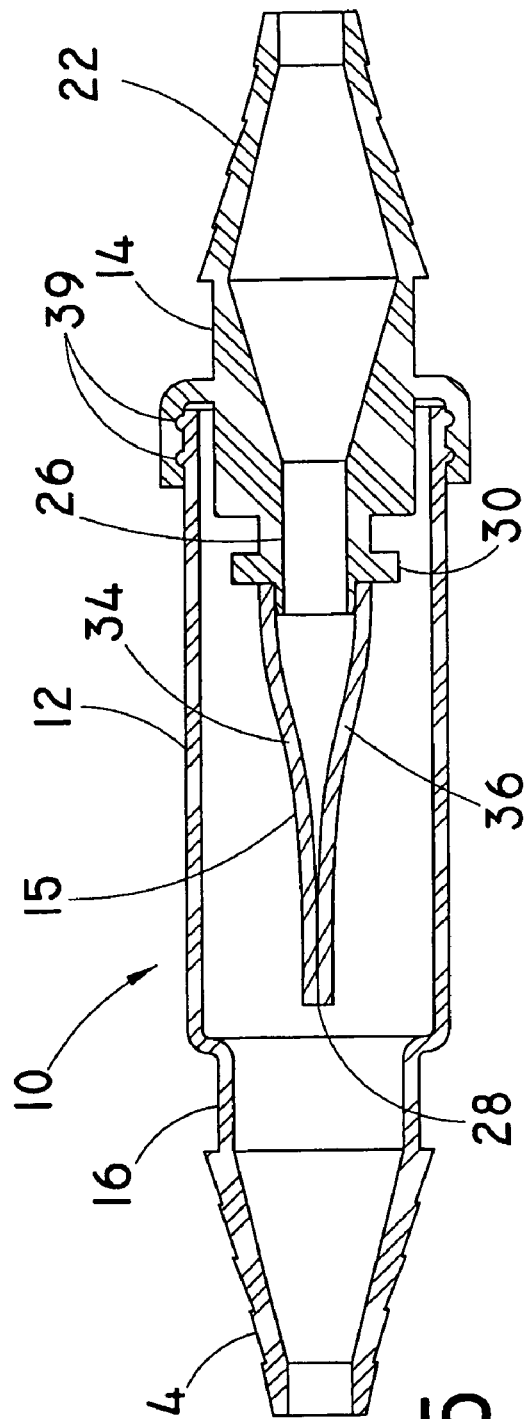

ONE-WAY MEDICAL VALVE APPARATUS

RELATED APPLICATIONS

The present patent document claims the benefit of the filing date under 35 U.S.C. §119(e) of Provisional U.S. Patent Application Ser. No. 60/589,676, filed Jul. 21, 2004, which is hereby incorporated by reference.

BACKGROUND

1. Technical Field

The present invention is directed to valves used in medical procedures, and more particularly, to a one-way valve apparatus that is structured to permit the passage of fluids in one direction only during a medical procedure, or as a consequence of a medical procedure.

2. Background Information

One-way medical valves are used in medicine for a variety of procedures involving drainage of fluids from the patient, and/or the infusion of fluids into the patient. The use of such valves is important in situations wherein the reflux or backflow of fluids can cause complications to the patient during or following a medical procedure, as well as in situations where the inflow of a fluid, such as air, can cause an unwanted and potentially harmful dilation of a particular part of a patient's anatomy.

For optimal use, it is important that such one-way valves be capable of operating in the physiological range. The valves should be capable of operating consistently at very low pressures while encountering a range of biological fluids. The valves should also be substantially unaffected by fluids and particles in the fluids, so that the valves do not stick in the closed position, thereby preventing the free flow of fluids therethrough.

One-way valves are often used in medical procedures where it is necessary to continuously drain fluid from an affected area. One especially important use for such valves is as a chest drain valve used for pneumothoraces. To be useful for chest drainage, it is important that the valve be structured to permit fluid to continuously drain through the valve. The valve must also be able to remain reliably closed when not draining fluid, in order to prevent the influx of air through the valve and into the chest cavity.

Devices for draining the chest cavity are known in the art. For example, it has been known to insert a drainage tube into the chest to establish a connection with a drainage apparatus. In order to avoid the possibility of reversal of flow of the drained fluid or the inadvertent disconnection of the drainage conduits, a relatively cumbersome drainage apparatus that included fluid traps and receptacles was positioned near the patient's bed. Although the drainage procedure with such a device was generally successful, the use of the cumbersome apparatus required that the drainage procedure not be interrupted. As a result, the patient was generally confined to the bed in order to avoid such interruption or interference with the drainage process.

An improved device for draining the chest cavity was described in U.S. Pat. No. 3,463,159 to Heimlich. This patent is incorporated by reference herein. This device is smaller than previously existing devices, and is also portable so that the patient need not be confined to a bed. The Heimlich device was formed of a generally cylindrical chamber made from a rigid plastic. The chamber houses a rubbery latex-type valve material. The valve material is open at one end to permit the entry of the fluid, and includes flattened walls at its outlet end. The flattened walls are separable to allow fluid and non-fluid particles to drain from the chest through a passage between the walls. At all other times, the walls are yieldably urged into a flattened condition to close the passage and prevent the undesired reverse flow of air and other materials into the chest cavity.

Although the Heimlich valve has a favorable overall configuration for fluid drainage, the device is still somewhat larger and more unwieldy than desired. In addition, the rubbery valve has a propensity to stick closed when biological fluids dry in the valve passage. Another problem with this and other prior art valves is that such devices are generally formulated from compounds, such as latex, which have been linked to allergic reactions in some individuals. In addition, latex valves are somewhat reactive to certain body materials, such as proteins. These materials may stick to the valve, and may cause the valve to stick in the closed position. Therefore, in order to minimize this possibility, it is often necessary to add talc to such valves. Also, since latex is a hydrophilic material, latex valves are prone to pick up water and swell. Use of a hydrophilic material runs counter to the purpose of the device, which is to provide a conduit to eliminate fluids from the system.

Another disadvantage of prior art valves, such as the valve described in Heimlich, is that the valves are frequently formed from a round tube that is pressed into a flat configuration. This arrangement generally leaves a gap at each of the edges of the mouth of the valve. These gaps may permit the unintended leakage of fluid even when the valve is closed.

What is desired is a valve that is compact, that effectively prevents the undesired backflow of fluids, that is formed from compounds which are substantially nonreactive to the fluids being drained or injected therethrough, and that minimizes the possibility of inadvertent leakage through the valve.

BRIEF SUMMARY

The present invention addresses the problems of the prior art. In one form thereof, the invention comprises a one-way valve apparatus for use in draining fluid from a patient. The one-way valve apparatus comprises a housing having an inlet end and an outlet end, and a valve positioned in the housing. The valve has an inlet end, an outlet end and a fluid pathway extending therebetween. The valve inlet end is engaged with the housing inlet end to comprise an open valve inlet end for receiving the fluid to be drained. The valve outlet end is in a normally closed position and is adapted to partially open to permit drainage of fluid received through the pathway from the inlet end, and to return to the normally closed position upon drainage of the fluid. The valve outlet end communicates with the housing outlet end such that the drained fluid passes from the valve outlet end through the housing outlet end.

In another form, the present invention comprises a method of forming a one-way valve apparatus for draining fluid from a patient. A housing member is provided having an inlet end, an outlet end and a valve-receiving space therebetween. First and second generally flat elongated members are provided, each of which includes longitudinal edges capable of registry with the longitudinal edges of the other of elongated member. The elongated members are sized to be received in the valve-receiving space. The longitudinal edges of the respective first and second elongated members are aligned in a manner such that the longitudinal edges of one of the elongated members engage the longitudinal edges of the other elongated member. The longitudinal edges of the aligned first and second elongated members are then joined by means such as welding by the transmission of radiofrequency energy to comprise a valve member. The inlet end of the valve member is engaged with the housing inlet end in the valve-receiving space.

In still another form, the present invention comprises a one-way valve apparatus for use in draining fluid from a patient, wherein the valve apparatus comprises a housing having an inlet end, an outlet end and a valve-receiving chamber therebetween, and an elastomeric valve positioned in the chamber. The valve has an inlet end, an outlet end and a fluid pathway extending therebetween. The elastomeric valve comprises a member selected from the group consisting of polyurethane, polyvinyl chloride, polyester, polyethylene, polyamide, silicone, polyisoprene, and preferably comprises a polyether-based polyurethane. The valve comprises first and second generally flat elongated members joined along respective longitudinal edges thereof. The valve inlet end is engaged with the housing inlet end to comprise an open valve inlet end for receiving the fluid to be drained. The valve outlet end is in a normally closed position, and is adapted to partially open to permit drainage of fluid received through the pathway from the inlet end, and to return to the normally closed position upon drainage of the fluid. The valve outlet end communicates with the housing outlet end such that the drained fluid passes from the valve outlet end through the housing outlet end. The valve may also include a lubricious filler and/or a lubricous coating.

BRIEF DESCRIPTION OF THE DRAWINGS

FIG. 4 is a sectional view taken along line 4-4 of FIG. 2;

FIG. 5 is a sectional view taken along line 5-5 of FIG. 3;

DETAILED DESCRIPTION OF THE DRAWINGS AND THE PRESENTLY PREFERRED EMBODIMENTS

Figure 1:
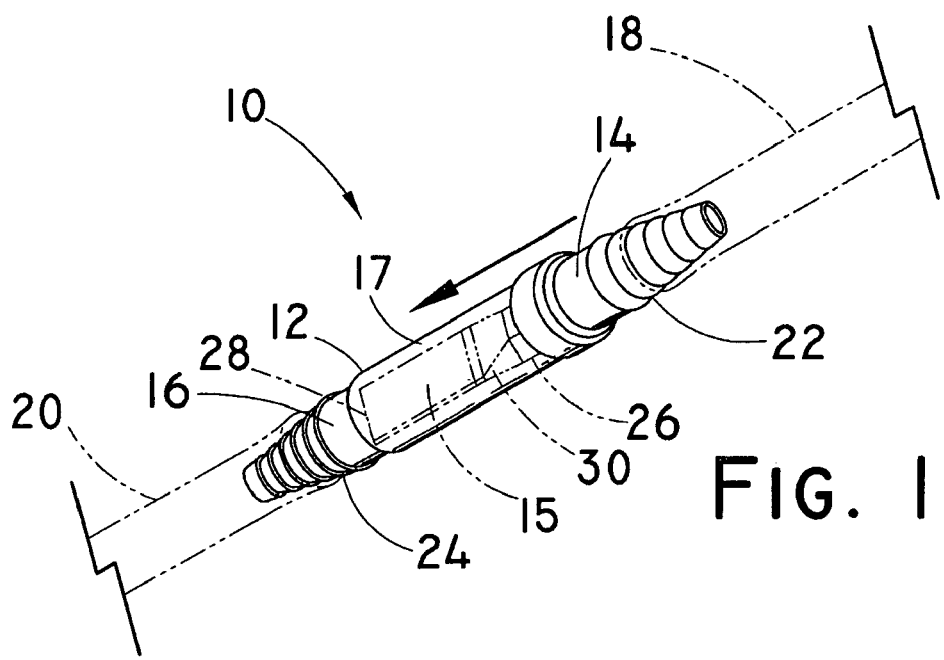
FIG. 1 is a perspective view of a one-way valve apparatus according to an embodiment of the present invention.
Figure 2:
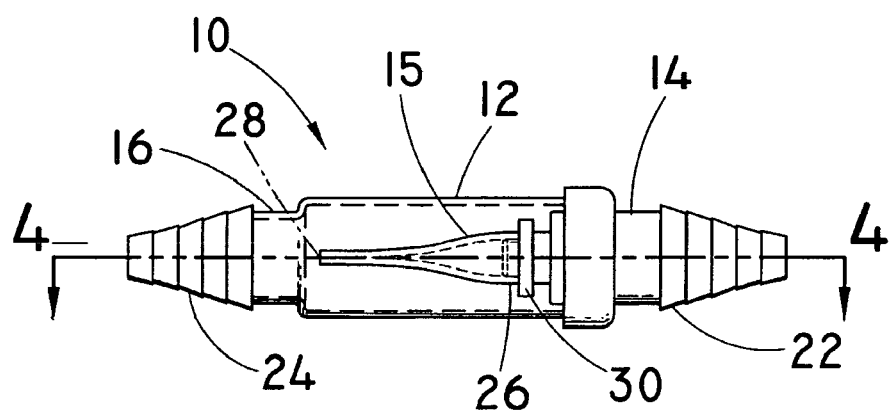
FIG. 2 is a side view of the one-way valve apparatus of FIG. 1.
Figure 3:
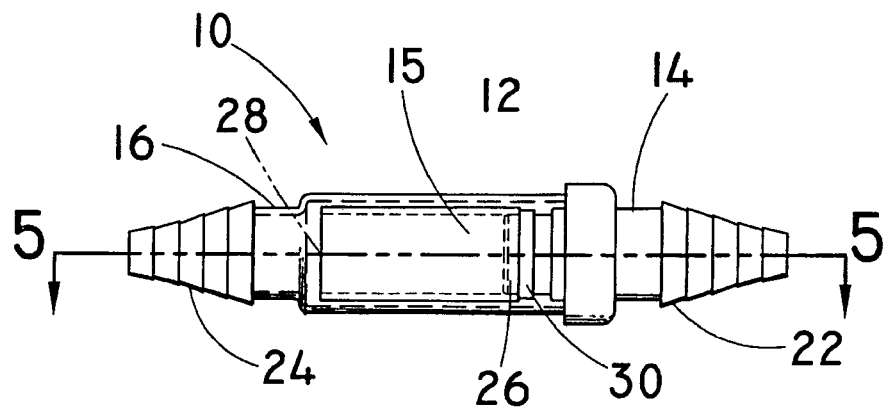
FIG. 3 is a top view of the one-way valve apparatus of FIG. 1.

For purposes of promoting an understanding of the present invention, reference will now be made to the embodiments illustrated in the drawings, and specific language will be used to describe the same. It is nevertheless to be understood that no limitation of the scope of the invention is thereby intended, the proper scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein. Common reference numerals used in the various figures denote the same element.

FIGS. 1-6 illustrate one embodiment of a one-way valve apparatus 10 according to an embodiment of the present invention. Apparatus 10 comprises a generally cylindrical housing 12 having an inlet 14, an outlet 16, and a valve-receiving chamber 17 extending therebetween. A valve 15 extends longitudinally from inlet 14 in the direction of outlet 16. Fluid and other materials are discharged through valve apparatus 10 from right to left in the orientation of the apparatus shown in the figures. Direction of flow is also indicated by the arrow in FIG. 1.

A funnel adapter 22, 24 is provided at each end of housing 12 for connection to respective inlet and outlet tubing 18, 20. Inlet 14 is connected via funnel adapter 22 in substantially leakproof fashion to a conventional inlet tube 18. Inlet tube 18 extends into the chest cavity of a patient in conventional fashion to receive fluids and other particles to be discharged from the patient's chest cavity. Outlet 16 is connected via funnel adapter 24 in substantially leakproof fashion to a conventional discharge tube 20. Discharge tube 20 receives the fluids and particles after they pass through valve 15, and serves as a conduit through which the fluids and particles pass prior to discharge into a suitable waste receptacle (not shown).

Valve 15 includes valve inlet end 26 and valve outlet end 28. Inlet end 26 of valve 15 surrounds nipple 30 or other suitable connector in conventional fashion to form an inlet opening of valve 15. In the embodiment shown, outlet end 28 of valve 15 terminates just short of the distal end of cylindrical housing 12.

Respective longitudinal and transverse sectional views of apparatus 10 are shown in FIGS. 4 and 5. These figures better illustrate valve inlet end 26 and valve outlet end 28. Valve inlet end 26 is shown engaged with nipple 30. If desired, an elongated end of valve inlet end 26 can be stretched over nipple 30 for a more secure attachment. Valve 15 comprises elongated valve sections 34, 36 (FIG. 5), that are joined along their longitudinal edges in a manner to be described.

Preferably, housing 12 is formed of a clear impact resistant material, such as a polycarbonate, so that valve 15 is visible therethrough. Valve 15 is preferably formed from a suitable elastomeric material such as a polyurethane, and more preferably a polyether-based polyurethane. An example of a particularly preferred polyether-based urethane is Pellethane® 2363, available from Dow Plastics. Other suitable valve materials include, but are not limited to, polyvinyl chloride, polyesters, polyethylenes, polyamides, silicone and polyisoprenes. Other non-limiting polymer classes that are also suitable for formation of the valve include Styrene Butadiene Styrene (SBS) polymers such as Kraton®, Dynaflex® and Santoprene®, vinyl compounds, silicone rubber materials such as poly-dimethyl siloxane, thermoplastic polyester elastomers (TPEs), and polyether block amides such as Pebax®.

Preferably, the valve material has a substantially non-stick surface that permits fluids and other materials to readily pass through the valve. Although the valve composition may provide satisfactory lubricity for routine use of the valve, lubricity may be further improved by the addition of one or more lubricity agents. For example, the formulation of the base valve material may be modified to include a lubricous filler compound, such as polyethylene glycol. Other preferred fillers include, for example, fatty acid amides, such as oleamide, erucamide and stearamide. Alternatively, lubricity can be imparted by bonding a suitable group onto the polymer chain. One non-limiting example includes the use of synthetic resins such as silicone poly-etherurethane, available from Polymer Technology Group of Berkeley, Calif., and sold under the trademark PurSil®. As another alternative, a suitable lubricious compound can be coated or covalently linked to the surface of the valve. One example of a suitable coating compound is a thin-film polymer such as parylene. As yet another alternative, a grafted co-polymer can be used to impart lubricity. These recited mechanisms for imparting lubricity may be applied individually, or in any combination. Those skilled in the art can readily determine other appropriate fillers and coating agents and methods that are suitable for imparting lubricity.

If desired, valve 15 may be still further modified to enhance its non-stick properties by providing a texture on either or both of the respective inner surfaces of valve sections 34, 36. Texturing of the valve surfaces can be done in combination with, or in the absence of, lubricous fillers or coatings. Typically, texturing will be accomplished by suitable treatment of the surface of the mold in which the valve sheets are formed. This is performed, for example, by etching a microsurface in the tool steel by known means such as abrasive grit microblasting. A cross-hatch pattern using diamond particles will produce micro-lines that become slight linear elevations when the sheet is formed. Those skilled in the art can readily determine an appropriate process for imparting texturing to a valve surface.

Figure 6:
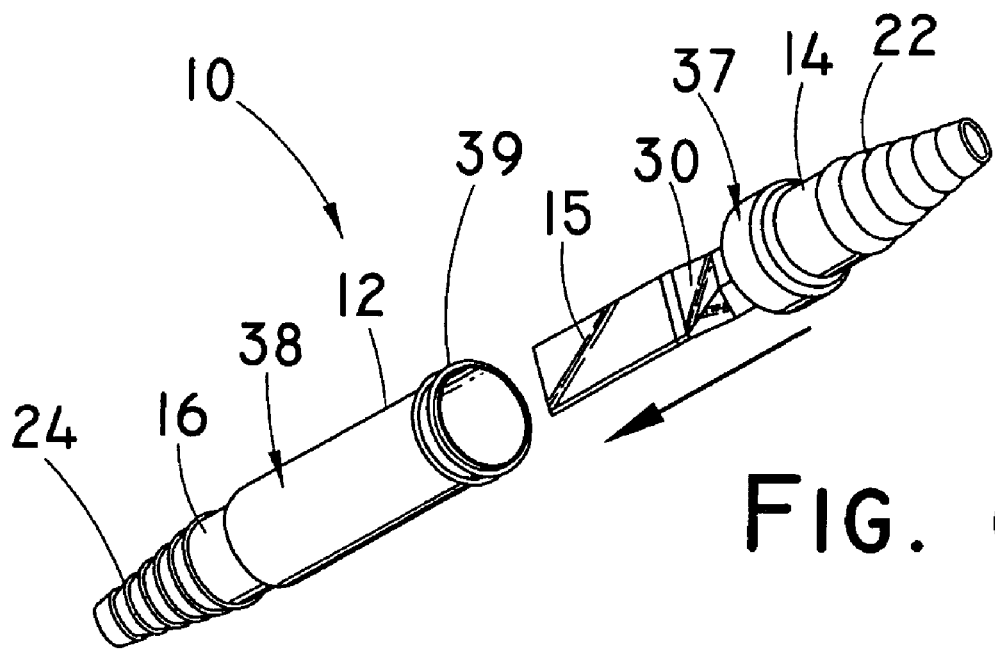
FIG. 6 is a perspective view of the one-way valve apparatus, showing the valve member prior to incorporation into the assembly.

Preferably, housing 12 of the apparatus is formed from two housing segments 37, 38, shown in FIG. 6. In this manner, once valve 15 is fitted on nipple 30, housing segment 37 can be engaged with housing segment 38 in any conventional fashion, such as by a snap fit. In this embodiment, housing segment 38 is provided with one or more annular ridges 39 that are sized and shaped to form a snap fit in conventional fashion with complementary receptacles and/or ridges in housing segment 37. Housing segment 37 need not necessarily be formed of a clear material, since valve 15 is normally visible through the portion of housing denoted as segment 38. In the examples shown, inlet 14 and funnel adapter 22 are integral on housing segment 37, and inlet 16 and funnel adapter 24 are integral on housing segment 38. Those skilled in the art will appreciate that there are numerous possible ways that the inlets and funnel adapters may be combined, and that the present invention is not limited to any specific arrangement.

In a preferred embodiment, valve 15 is formed from two flat sheets of elastomeric material as described. When the valve is formed in the manner to be described, the flat sheets comprise valve sections 34, 36. During formation of valve 15, two identical sheets of elastomeric material of the desired size and shape for the size of the valve to be formed may initially be placed one on top of the other. The sheets are joined together along their longitudinal edges 35, leaving the transverse edges free to allow passage of the material to be drained. One particularly preferred way to accomplish the joinder of these valve edges is by welding the longitudinal ends, such as by the transmission of radiofrequency energy. When radiofrequency energy is used, the RF energy can be directed to very specific areas of the valve to form a very thin seam. The resulting weld is as strong as the sheet from which it was derived. Such techniques are well known to those skilled in the art. Alternatively, the longitudinal seam can be formed by other means known in the art, such as gluing, induction bonding, ultrasonic welding, solvent bonding, hot wire, heated die platen, insert molding and vibration fusion.

Figure 7:
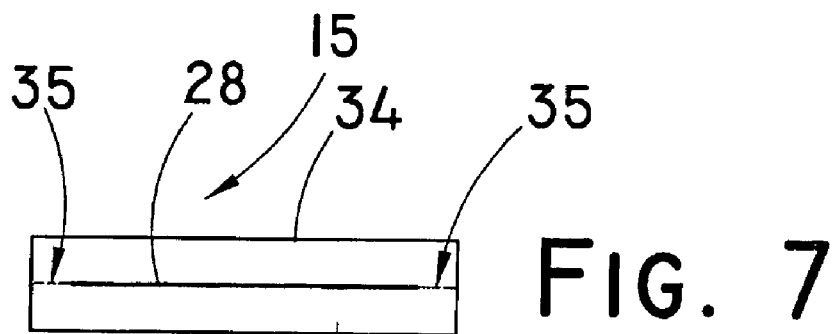
FIG. 7 is an end view of the outlet end of the valve portion of the inventive apparatus.
Figure 8:
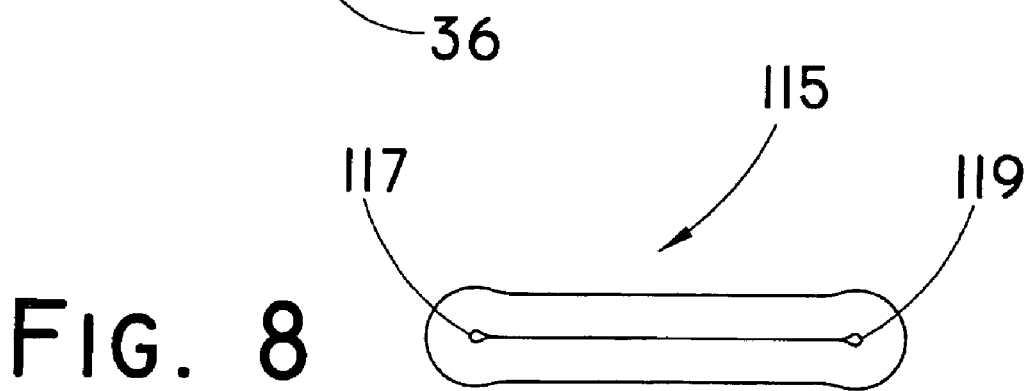
FIG. 8 is an end view of the outlet end of a prior art valve.

When a valve is formed of two sheets of material longitudinally joined as described, the valve has a very flat profile, which leads to enhanced sealing. The outlet end of such a valve is shown in FIG. 7. For purposes of comparison, a prior art valve 115 formed from a round tube that is pressed into a flat configuration is shown in FIG. 8. The valve of FIG. 8 includes gaps 117, 119 at the edges of the mouth of the valve, that are formed as the round tube is flattened. Such gaps are subject to leakage, and provide a pathway that may undesirably allow backflow through the valve in the direction opposite of the arrow. No such gaps are formed in the valve of FIG. 7, which is formed from two initially flat sheets longitudinally joined at their edges, as described.

Although not intending to be bound by dimensions, one embodiment of the inventive valve apparatus is formed to have a very compact shape. In this embodiment, the valve apparatus comprises approximately 2.75 inches (7 cm) from end 50 to end 52. Prior art valves are generally larger than this. In addition, the inventive apparatus is believed to be more crush resistant than existing assemblies.

One intended use of the valve apparatus 10 is to re-inflate lungs which have collapsed due to conditions such as a pneumothorax. If the pressure in the air in the pleural space (chest cavity) is higher than the air outside of the body (tension pneumothorax), the valve functions to expel air trapped in the pleural space through the valve. Once the pressure is equalized, the one-way valve functions to keep air from returning into the pleural space. The valve expels air when the patient coughs, thereby slowly re-expanding the lung by causing a negative pressure (vacuum) in the space.

It is therefore intended that the foregoing detailed description be regarded as illustrative rather than limiting, and that it be understood that it is the following claims, including all equivalents, that are intended to define the spirit and scope of this invention.

The invention claimed is:

1. A one-way valve apparatus for use in draining fluid from a patient, comprising:
    a housing having an inlet end, an outlet end and a valve-receiving chamber therebetween; and
    an elastomeric valve positioned in said chamber, said valve having an inlet end, an outlet end and a fluid pathway extending therebetween, said elastomeric valve comprising a member selected from the group consisting of polyurethane, polyvinyl chloride, polyester, polyethylene, polyamide, silicone, polyisoprene, or a blend of one or more of the foregoing, said valve comprising first and second initially flat elongated members, said first and second initially flat elongated members being joined along respective longitudinal edges thereof, said valve inlet end engaged with said housing inlet end to comprise an open valve inlet end for receiving said fluid to be drained, said valve outlet end being in a normally closed position and being adapted to partially open to permit drainage of fluid received through said pathway from said inlet end, and to return to said normally closed position upon drainage of said fluid, said valve outlet end communicating with said housing outlet end such that said drained fluid passes from said valve outlet end through said housing outlet end.

2. The apparatus of claim 1, wherein said valve is sized to substantially span said housing inlet and outlet ends.

3. The apparatus of claim 1, wherein said elastomeric member comprises a polyether-based polyurethane.

4. The apparatus of claim 1, wherein said valve comprises a lubricious filler.

5. The apparatus of claim 4, wherein said lubricious filler comprises polyethylene glycol or a fatty acid amide.

6. The apparatus of claim 1, wherein said valve comprises a lubricious coating.

7. The apparatus of claim 1, wherein said first and second members are joined along said respective longitudinal edges by welding.

8. The apparatus of claim 1, wherein said first and second generally flat elongated members each have an inner surface, and wherein the inner surface of at least one of said elongated members is textured.

9. The apparatus of claim 1, wherein said housing inlet end includes a nipple, and said valve inlet end is engaged with said housing inlet end at said nipple.

10. The apparatus of claim 1, wherein said housing comprises at least two housing segments.

11. The apparatus of claim 1, wherein said elastomeric valve comprises a polyether-based polyurethane, said valve further comprising at least one of a lubricious filler and a lubricious coating.

12. A method of forming a one-way valve apparatus for draining fluid from a patient, comprising:
   providing a housing, said housing having an inlet end, an outlet end and a valve-receiving space therebetween;
   providing first and second flat elongated members, each of said first and second elongated members having longitudinal edges capable of registry with longitudinal edges of the other of said elongated members, said first and second elongated members being sized to be received in said valve-receiving space;
   aligning said longitudinal edges of said respective first and second elongated members such that the longitudinal edges of one of said elongated members engage the longitudinal edges of the other of said elongated members;
   joining said longitudinal edges of said aligned first and second elongated members to comprise a valve member; and
   engaging an end of said valve member with said housing inlet end in said valve-receiving space.

13. The method of claim 12, wherein said longitudinal edges are joined by one or more of welding, gluing, induction bonding, solvent bonding, hot wire treatment, heated die platen, insert molding and vibration fusion.

14. The method of claim 13, wherein said longitudinal edges are welded by the transmission of radiofrequency energy to said edges.

15. The method of claim 12, wherein said valve member comprises an elastomer.

16. The method of claim 12, wherein said valve member comprises at least one of a lubricious filler and a lubricious coating.

17. The method of claim 12, wherein said valve member is engaged with said housing inlet end by engaging a nipple disposed on said housing inlet end.

\* \* \* \* \*